(12) United States Patent
Porco

(10) Patent No.: US 11,865,049 B2
(45) Date of Patent: Jan. 9, 2024

(54) EYE GLASS SHIELD DEVICE

(71) Applicant: Karrie Porco, Napean (CA)

(72) Inventor: Karrie Porco, Napean (CA)

( * ) Notice: Subject to any disclaimer, the term of this patent is extended or adjusted under 35 U.S.C. 154(b) by 92 days.

(21) Appl. No.: 17/580,242

(22) Filed: Jan. 20, 2022

(65) Prior Publication Data

US 2023/0225904 A1    Jul. 20, 2023

(51) Int. Cl.
*A61F 9/02* (2006.01)
*G02C 11/00* (2006.01)

(52) U.S. Cl.
CPC .............. *A61F 9/029* (2013.01); *G02C 11/12* (2013.01)

(58) Field of Classification Search
CPC . A61F 9/02; A61F 9/025; A61F 9/029; G02C 5/143; G02C 7/16; G02C 9/00; G02C 9/02; G02C 9/04; G02C 11/12
See application file for complete search history.

(56) References Cited

U.S. PATENT DOCUMENTS

| | | | | |
|---|---|---|---|---|
| 2,527,027 A * | 10/1950 | Mull | .................. | G02C 1/00 351/44 |
| 2,840,821 A | 7/1958 | Gay | | |
| 3,505,679 A | 4/1970 | Bennett | | |
| 4,271,538 A * | 6/1981 | Montesi | .................. | A61F 9/02 2/447 |
| 4,425,669 A * | 1/1984 | Grendol | .................. | A61F 9/028 2/436 |
| 4,877,320 A * | 10/1989 | Holden | .................. | G02C 11/12 351/44 |
| 4,964,714 A * | 10/1990 | Weymouth, Jr. | ........ | A61F 9/025 351/111 |
| 4,976,530 A * | 12/1990 | Mackay | .................. | G02C 9/00 351/44 |
| 5,319,396 A * | 6/1994 | Cesarczyk | .............. | G02C 7/16 351/124 |
| 5,321,443 A * | 6/1994 | Huber | ...................... | G02C 9/04 351/44 |
| 5,426,473 A * | 6/1995 | Riehm | .................. | G02C 5/146 351/149 |
| 5,614,963 A | 3/1997 | Parker | | |
| 5,943,114 A | 8/1999 | Grendelmeier | | |
| 6,557,995 B1 | 5/2003 | Edwards | | |
| 6,604,823 B2 * | 8/2003 | Hursey, Jr. | .............. | G02C 3/003 351/44 |
| 6,776,481 B2 | 8/2004 | Ng | | |
| 6,952,840 B2 * | 10/2005 | Chen | ...................... | A61F 9/025 2/449 |

(Continued)

FOREIGN PATENT DOCUMENTS

WO    WO2004023190    3/2004

*Primary Examiner* — F Griffin Hall

(57) ABSTRACT

An eye glass shield includes a goggle frame having a center. A lens is positioned in the center of the goggle frame and is constructed of a transparent material. A pair of temples comprising of a left temple and a right temple is coupled to the goggle frame. The left temple is coupled to a left edge of the goggle frame, and the right temple is coupled to a right edge of the goggle frame. A pair of temple clips is coupled to a respective one of the pair of temples. A top base is coupled to a top edge of the goggle frame and protruding there from. A bottom base is coupled to a bottom edge of the goggle frame and extending there from. A cut-out in the goggle frame creates a bridge in the top center of the goggle frame.

15 Claims, 4 Drawing Sheets

(56) References Cited

U.S. PATENT DOCUMENTS

| | | | | |
|---|---|---|---|---|
| 7,325,920 | B1* | 2/2008 | Gelfuso | G02C 3/02 |
| | | | | 2/10 |
| 7,556,374 | B1* | 7/2009 | Cooper | G02C 5/143 |
| | | | | 351/158 |
| D598,946 | S | 8/2009 | Roux | |
| 8,210,676 | B1* | 7/2012 | Hunt | G02C 9/04 |
| | | | | 2/209.13 |
| 8,840,244 | B2* | 9/2014 | Terry | G02C 3/006 |
| | | | | 351/121 |
| 9,442,312 | B2 | 9/2016 | Lee | |
| 11,547,607 | B2* | 1/2023 | Chin | A61F 9/029 |
| 2020/0222240 | A1* | 7/2020 | McManus | A61F 9/026 |
| 2022/0107513 | A1* | 4/2022 | Smith, III | G02C 11/10 |

* cited by examiner

EYE GLASS SHIELD DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to goggles and more particularly pertains to a new eye glass shield for attaching eye glass shield to eye glasses.

(2) Description of Related Art Including Information Disclosed Under 37 CFR 1.97 and 1.98

The prior art relates to eye glass shields for shielding eye glasses. The prior art discloses a variety of eye glass shields providing protection to the temples of the eye glasses. The prior art also relates to a variety of eye glass shields being attached having a goggle base frame being attached to the frame of the glasses. There is no mentioning in the prior art that discloses an eye glass shield having a goggle frame coupled to a pair of temples that attach to the temples of the eye glasses by a pair of temple clips.

BRIEF SUMMARY OF THE INVENTION

An embodiment of the disclosure meets the needs presented above by generally comprising a goggle frame having a center. The goggle frame has a left edge and a right edge. The goggle frame has a top edge and a bottom edge. A pair of temples comprising of a left temple and a right temple. The left temple is coupled to the left edge and protruding out from the left edge. The right temple is coupled to the right edge and protruding out from the right edge. A pair of temple clips; each temple clip of the pair of temple clips is coupled to a respective one of the pair of temples. A top base is coupled to the top edge of the goggle frame. The top base is extending out from the top edge. A bottom base is coupled along the bottom edge of the goggle frame. The bottom base is protruding out from the bottom edge. A cut-out creates a bridge positioned in a top center of the goggle frame.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
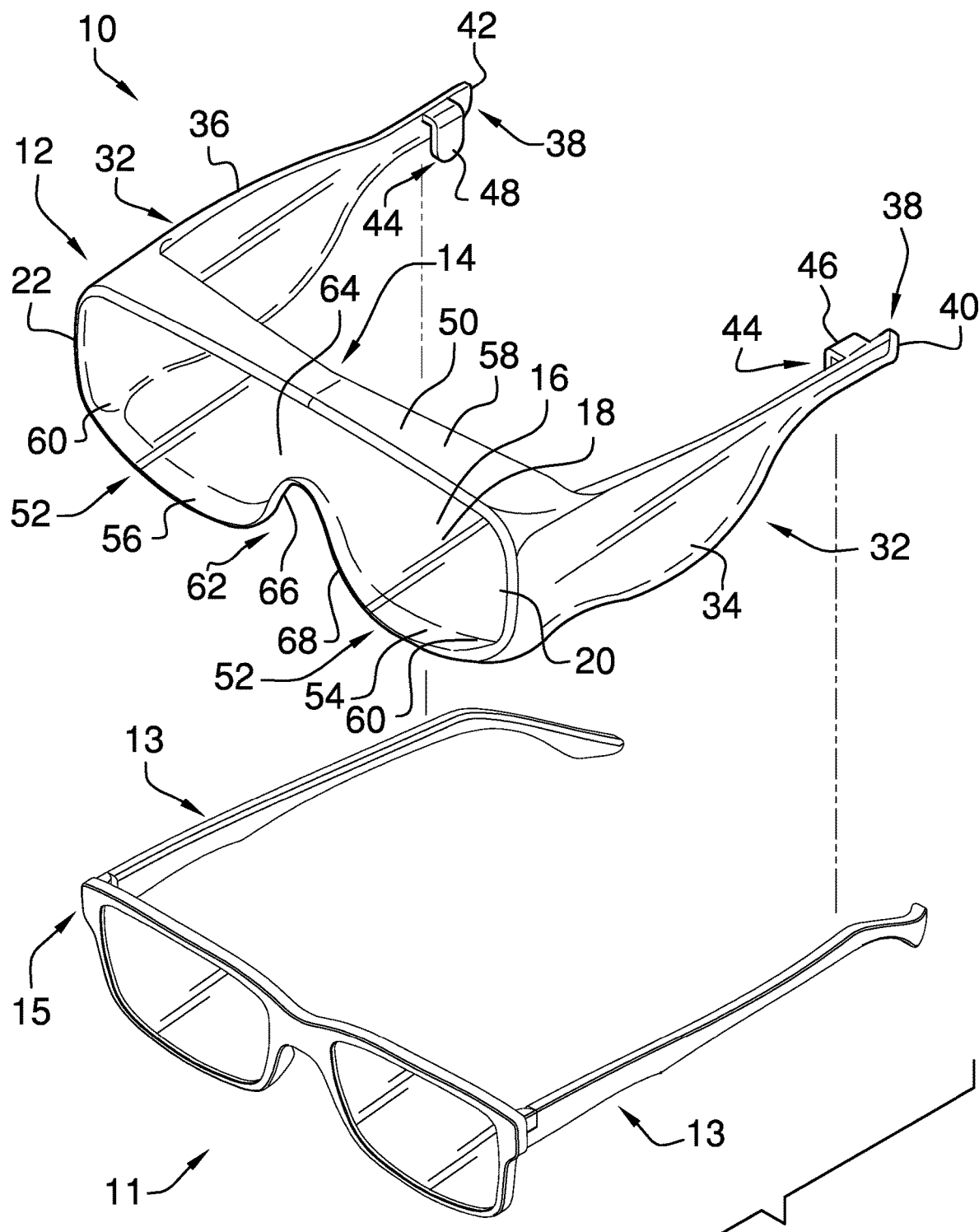
FIG. 1 is an isometric view of an eye glass shield device according to an embodiment of the disclosure.

With reference now to the drawings, and in particular to FIGS. 1 through 6 thereof, a new eye glass shield embodying the principles and concepts of an embodiment of the disclosure and generally designated by the reference numeral 10 will be described.

Figure 2:
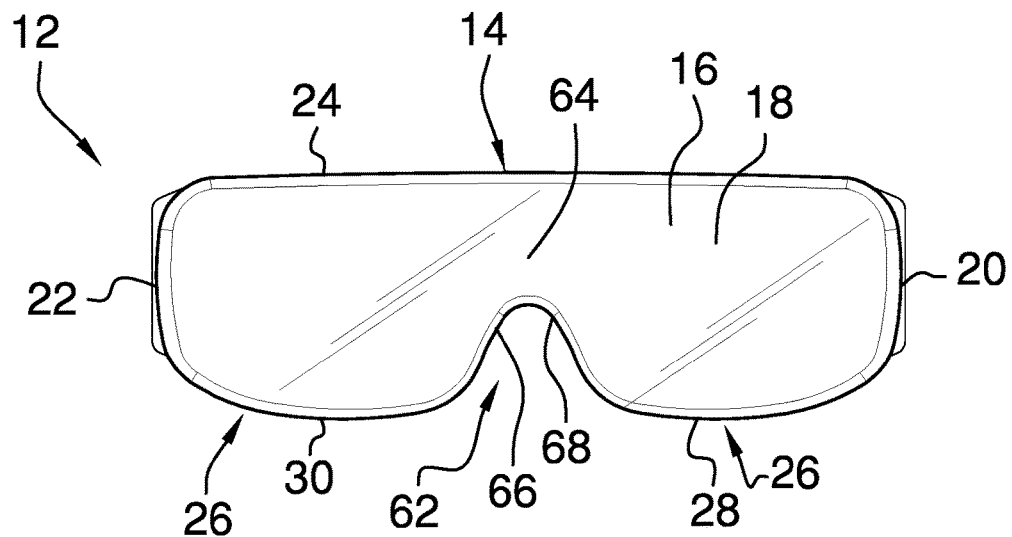
FIG. 2 is a front view of an embodiment of the disclosure.

As best illustrated in FIGS. 1 through 5, the eye glass shield device 10 generally comprises a goggle frame 12 having a center 14. A lens 16 is positioned in the center 14 of the goggle frame 12. The lens 16 is constructed of a transparent material 18. The goggle frame 12 has a left edge 20 and a right edge 22. The left edge 20 and the right edge 22 are positioned parallel to each other as shown in FIG. 2.

The goggle frame has a top edge 24 and a bottom edge 26. The bottom edge 26 comprises of a left side 28 of the bottom edge 26 and a right side 30 of the bottom edge 26. The top edge 24 and the bottom edge 26 are positioned parallel to each other. Shown in FIG. 2, the top edge 24 and bottom edge 26 are positioned perpendicular to the left edge 20 and the right edge 22.

Figure 4:
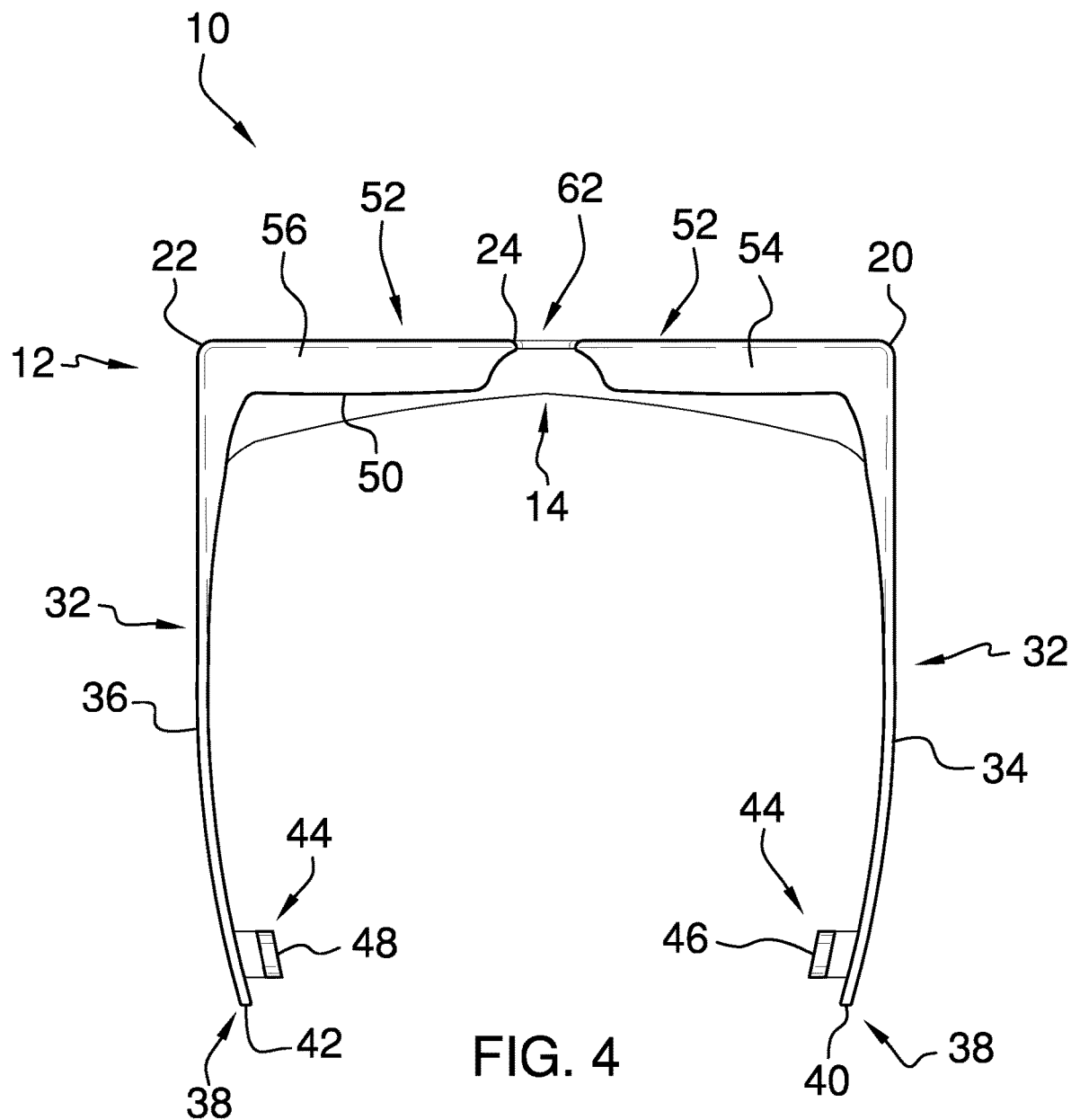
FIG. 4 is a bottom view of an embodiment of the disclosure.

A pair of temples 32 comprising of a left temple 34 and a right temple 36 are coupled to the goggle frame 12. The left temple 34 is coupled to the left edge 20 and protruding out from the left edge 20. The right temple 36 is coupled to the right edge 22 and protruding out from the right edge 22 as shown in FIG. 4.

Each temple of the pair of temples 32 has a tip 38. The left temple 34 has a left tip 40, and the right temple 34 has a right tip 42. The tip 38 is a distal end of each temple of the pair of temples 32 relative to the goggle frame 12. The tip 38 is a free end of each temple 32. The tip 38 lacks any structural connection to other elements.

A pair of temple clips 44 is coupled to a respective one of the pair of temples 32. The pair of temple clips 44 comprises of a left temple clip 46 and a right temple clip 48. The left temple clip 46 is coupled to the left temple 34, and the right temple clip 48 is coupled to the right temple 36. Each clip of the pair of temple clips 44 is positioned proximate to the tip 38 of each temple of the pair of temples 32 as shown in FIG. 4.

A top base 50 is coupled to the top edge 24 of the goggle frame 12 and protruding there from. A bottom base 52 is coupled to the bottom edge 26 of the goggle frame 12 and extending there from. The bottom base 52 comprises of a left side of the bottom base 54 and a right side of the bottom base 56. The top base 50 has a flat surface 58. The bottom base 52 has a beveled surface 60 relative to the bottom edge 26. The top base 50 and the bottom base 52 are positioned perpendicular relative to the left edge 20 and the right edge 22 of the goggle frame 12.

A cut-out 62 creates a bridge 64 in the center 14 of the goggle frame 12. The cut-out 62 has an arch shape 66, and provides a space 68 for a nose of the user 70 to be placed in. The bridge 64 is secured in place on top of the nose of the user 70.

Figure 3:
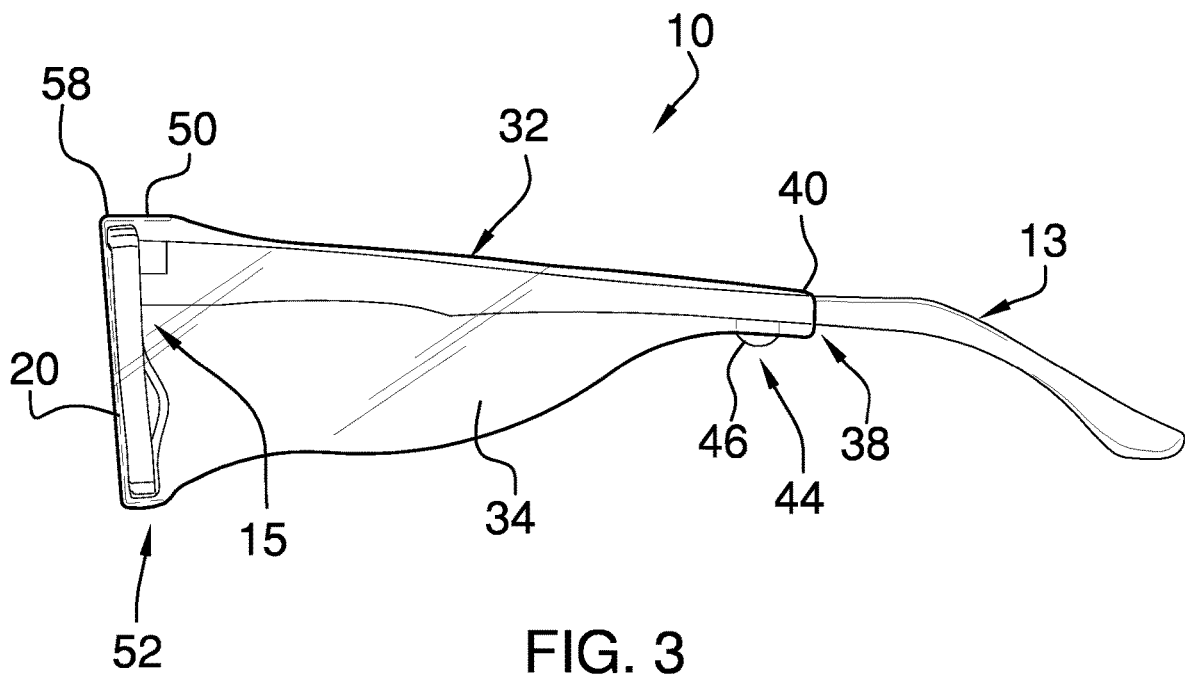
FIG. 3 is a side in-use view of an embodiment of the disclosure.
Figure 5:
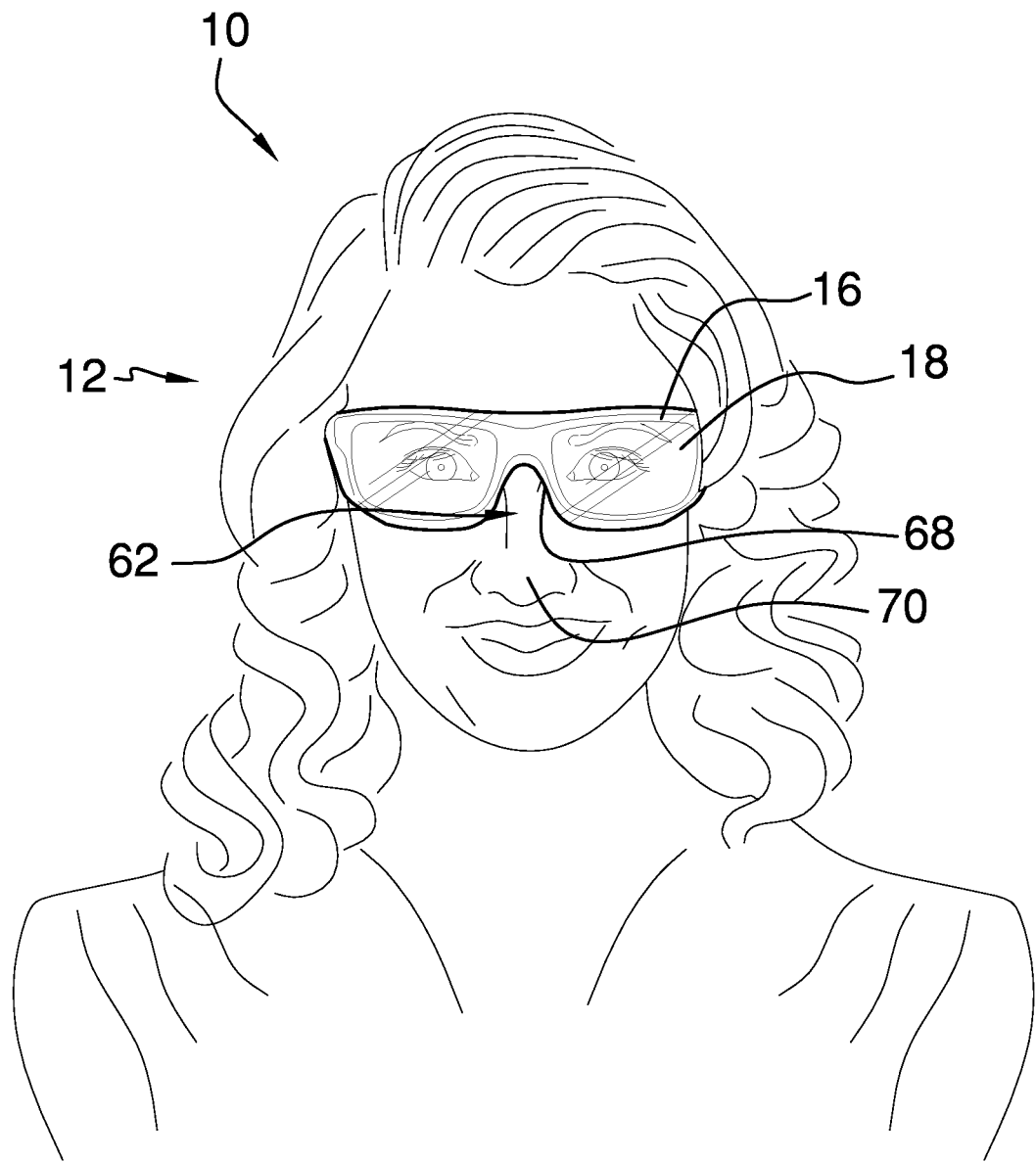
FIG. 5 is a front in-use view of an embodiment of the disclosure.

In use, the eye glass shield device 10 is attached to the eye glasses 11. Each clip of the pair of temple clips 44 attaches to the temples 13 of the eye glasses as shown in FIG. 3. The frame 15 of the eye glasses 11 is placed adjacent to the goggle frame 12 as shown in FIG. 3. The top base 50 shields the top of the frame 15 of the eye glasses 11, and the bottom base 52 shields the bottom of the frame 15 of the eye glasses 11. The bridge 64 in the center 14 of the goggle frame 12 is placed on a nose of the user 70 as shown in FIG. 5.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An eye glass shield device comprising:
    a goggle frame, said goggle frame having a center, said goggle frame having a left edge and a right edge, said goggle frame having a top edge and a bottom edge;
    a pair of temples, said pair of temples comprising of a left temple and a right temple, said left temple being coupled to said left edge and protruding out from said left edge, said right temple being coupled to said right edge and protruding out from said right edge;
    a pair of temple clips, each temple clip of said pair of temple clips being coupled to a respective one of said pair of temples, said pair of temple clips being positioned on said pair of temples such that said temple clips are configured to engage each temple of the eye glasses wherein said temple clips secure said goggle frame to the eye glasses, each temple clip of said pair of temple clips being positioned proximate to a respective one of a pair of tips of said pair of temples, each temple clip being L-shaped having a first flange extending perpendicularly from a fixed position on said respective one of said pair of tips of said pair of temples, each temple clip having a second flange extending perpendicularly and downwardly from said first flange;
    a top base, said top base being coupled to said top edge of said goggle frame, said top base extending out from said top edge;
    a bottom base, said bottom base being coupled along said bottom edge of said goggle frame, said bottom base protruding out from said bottom edge; and
    a cut-out, said cut-out creating a bridge positioned in a top center of said goggle frame.

2. The eye glass shield device of claim 1, further comprising a lens frame being positioned in said center of said goggle frame.

3. The eye glass shield device of claim 2, further comprising said lens frame being constructed of a transparent material.

4. The eye glass shield device of claim 1, further comprising said left edge and said right edge being positioned parallel relative to each other.

5. The eye glass shield device of claim 1, further comprising said top edge and said bottom edge being positioned perpendicular relative to said left edge and said right edge.

6. The eye glass shield device of claim 5, further comprising said top edge being flat.

7. The eye glass shield device of claim 1, further comprising said goggle frame being a color.

8. The eye glass shield device of claim 1, further comprising said left temple and said right temple being perpendicular relative to said top edge of said goggle frame.

9. The eye glass shield device of claim 1, further comprising said pair of temples being a color.

10. The eye glass shield device of claim 1, further comprising said top base being coupled to said top edge along a full length of said top edge, said top base having a flat surface.

11. The eye glass shield device of claim 10, further comprising said top base being perpendicular relative to said left edge and said right edge of said goggle frame, wherein said top base is configured for shielding a top of the pair of eye glasses.

12. The eye glass shield device of claim 1, further comprising said bottom base being coupled along an entire length of said bottom edge, said bottom base having a curvature surface relative to said bottom edge.

13. The eye glass shield device of claim 12, further comprising said bottom base being positioned parallel relative to said top base of said goggle frame, wherein said bottom base is configured for shielding a bottom of the pair of eye glasses.

14. The eye glass shield device of claim 1, further comprising said cut out having a shape of an arch, wherein said cut-out is configured for placement on a nose.

15. An eye glass shield device comprising:
    a goggle frame, said goggle frame having a center, a lens frame being positioned in said center of said goggle frame, said lens frame being constructed of a transparent material, said goggle frame having a left edge and a right edge, said left edge and said right edge being positioned parallel relative to each other, said goggle frame having a top edge and a bottom edge, said top edge and said bottom edge being positioned perpendicular relative to said left edge and said right edge, said top edge and said bottom edge being positioned parallel relative to each other, said top edge being flat, said goggle frame being a color;

a pair of temples, said pair of temples comprising of a left temple and a right temple, said left temple being coupled to said left edge and protruding out from said left edge, said right temple being coupled to said right edge and protruding out from said right edge, said left temple and said right temple being perpendicular relative to said top edge of said goggle frame, each tip of a pair of tips being a free end respective to one of said pair of temples, said pair of temples being a color;

a pair of temple clips, each temple clip of said pair of temple clips being coupled to a respective one of said pair of temples, said pair of temple clips being positioned on said pair of temples such that said temple clips are configured to engage each temple of the eye glasses wherein said temple clips secure said goggle frame to the eye glasses, each temple clip of said pair of temple clips being positioned proximate to a respective one of said pair of tips of said pair of temples, each temple clip being L-shaped having a first flange extending perpendicularly from a fixed position on said respective one of said pair of tips of said pair of temples, each temple clip having a second flange extending perpendicularly and downwardly from said first flange;

a top base, said top base being coupled to said top edge of said goggle frame, said top base being coupled to said top edge along a full length of said top edge, said top base extending out from said top edge, said top base having a flat surface, said top base being perpendicular relative to said left edge and said right edge of said goggle frame, wherein said top base is configured for shielding a top of the pair of eye glasses;

a bottom base, said bottom base being coupled along said bottom edge of said goggle frame, said bottom base being coupled along an entire length of said bottom edge, said bottom base protruding out from said bottom edge, said bottom base having a curvature surface relative to said bottom edge, said bottom base being positioned parallel relative to said top base of said goggle frame, wherein said bottom base is configured for shielding a bottom of the pair of eye glasses; and a cut-out, said cut out having a shape of an arch, said cut-out creating a bridge positioned in a top center of said goggle frame, wherein said cut-out is configured for placement on a nose.

\* \* \* \* \*